United States Patent [19]
Wynn

[11] Patent Number: 5,137,738
[45] Date of Patent: Aug. 11, 1992

[54] SYSTEM AND METHOD FOR CONTROLLING BUTTERFAT CONTENT IN STANDARDIZED MILK PRODUCT USING WHOLE PRODUCT SENSOR

[75] Inventor: William H. Wynn, Hillsborough, Calif.

[73] Assignee: Wedgewood Technology, Inc., San Carlos, Calif.

[21] Appl. No.: 686,586

[22] Filed: Apr. 17, 1991

Related U.S. Application Data

[63] Continuation-in-part of Ser. No. 352,259, May 16, 1989, Pat. No. 5,009,794.

[51] Int. Cl.⁵ .................................................. A23C 9/00
[52] U.S. Cl. ...................................... 426/231; 99/452; 356/436; 426/491; 426/580; 210/745
[58] Field of Search ............... 99/452, 456; 210/85, 210/94, 96.1, 143, 739, 745, 790; 356/36, 436, 44 E; 426/231, 491, 580, 586

[56] References Cited

U.S. PATENT DOCUMENTS

| | | | |
|---|---|---|---|
| 2,752,815 | 7/1956 | Batchelor | 356/36 |
| 3,946,113 | 3/1976 | Seiberling | 426/586 |
| 3,983,257 | 9/1976 | Malmberg et al. | 426/231 |
| 4,017,643 | 4/1977 | Lester | 426/231 |
| 4,074,622 | 2/1978 | Niemeyer | 426/586 |
| 4,075,355 | 2/1978 | Pató | 426/231 |
| 4,144,804 | 3/1979 | O'Keefe et al. | 426/231 |

FOREIGN PATENT DOCUMENTS 197704  4/1977  U.S.S.R. ............................ 426/231

Primary Examiner—Robert A. Dawson
Assistant Examiner—Joseph Drodge
Attorney, Agent, or Firm—Flehr, Hohbach, Test, Albritton & Herbert

[57] ABSTRACT

System and method for controlling the content of a fluid product such as milk. The entire product stream is monitored continuously, and the actual content of the stream is compared with the desired content. A correction signal which varies in accordance with the difference between the actual content and the desired content is provided, and in one disclosed embodiment the content of the product is adjusted in response to the correction signal by an amount which decreases as the content approaches the desired level. In another disclosed embodiment, the butterfat content of both the standardized milk product and an excess cream output are controlled. The correction signals are adapted to control valves which control flow to result in both the standardized milk product and excess cream output having the desired butterfat content.

20 Claims, 5 Drawing Sheets

SYSTEM AND METHOD FOR CONTROLLING BUTTERFAT CONTENT IN STANDARDIZED MILK PRODUCT USING WHOLE PRODUCT SENSOR

This is a continuation-in-part of Ser. No. 07/352,259, filed May 16, 1989, now U.S. Pat. No. 5,009,794.

This invention pertains generally to the standardization of a fluid product having constituent parts and, more particularly, to a system and method for controlling the butterfat content of milk.

Raw milk contains a relatively large amount of butterfat in the form of cream, and the amount of cream varies with a number of factors such as the cows which give the milk, the feed eaten by the cows, and the season of the year.

In order to produce a milk product having a more uniform butterfat content, the raw milk is separated into low fat milk, or skim milk, and high fat milk, or cream. A portion of the high fat milk is then recombined with the low fat milk to provide a milk product having the desired fat content, e.g., 3%. The excess cream is drawn from the system and can be packaged separately or utilized in a milk product such as "half and half" or butter.

In processing milk in this manner, it is important to control the butterfat content accurately since that is what generally determines the food value and price of the product, as well as compliance with state and federal regulations. In the past, a number of techniques have been employed with varying degrees of success to control the butterfat content. In some systems, which can be thought of as "feed forward" systems, the amount of cream to be added to the skim milk is, in effect, calculated from factors such as the flow volumes of the raw milk input, the flow volumes of the skim milk or cream, and the fat content of the skim milk or cream. There is generally no provision in these systems for actually monitoring the fat content of the resulting product. Examples of such systems are found in U.S. Pat. Nos. 3,829,584, 3,946,113, 3,983,257, 4,075,355, U.K. Patent 1,435,984, Dutch Patent 7,407,130 (which corresponds to U.S. Pat. No. 3,983,257) and Soviet Patent 552,935.

In another type of system, which is sometimes referred to as a "feedback" system, samples of the product are taken from the output stream, and the amount of cream introduced into the product stream is adjusted to maintain a desired butterfat content in the output stream. Examples of this type of system are found in U.S. Pat. Nos. 4,017,643, 4,074,622, 4,144,804 and 4,145,450.

U.S. Pat. No. 2,752,815 discloses a system in which butterfat content is monitored with an optical sensor and displayed by a meter. An optical sensor is also employed in the system shown in U.S. Pat. No. 4,144,804.

It is in general an object of the invention to provide an new and improved system and method for controlling the content of a fluid product such as milk.

Another object of the invention is to provide a system and method of the above character which overcome the limitations and disadvantages of techniques heretofore employed.

Another object of the invention is to provide a system and method of the above character in which the butterfat content of a standardized milk product is more accurately controlled than in systems of the prior art.

These and other objects are achieved in accordance with the invention by providing a reference signal corresponding to a desired content in a product stream, monitoring the product stream and providing a signal corresponding to the actual content of the product, monitoring the reference signal and the actual content signal and providing a correction signal which varies in accordance with the difference between the actual content and the desired content, and adjusting the content of the product in response to the correction signal by an amount which, in one embodiment, decreases as the content of the product approaches the desired content. In another embodiment, the butterfat content of both the standardized milk product and an excess cream output are controlled.

Figure 1:
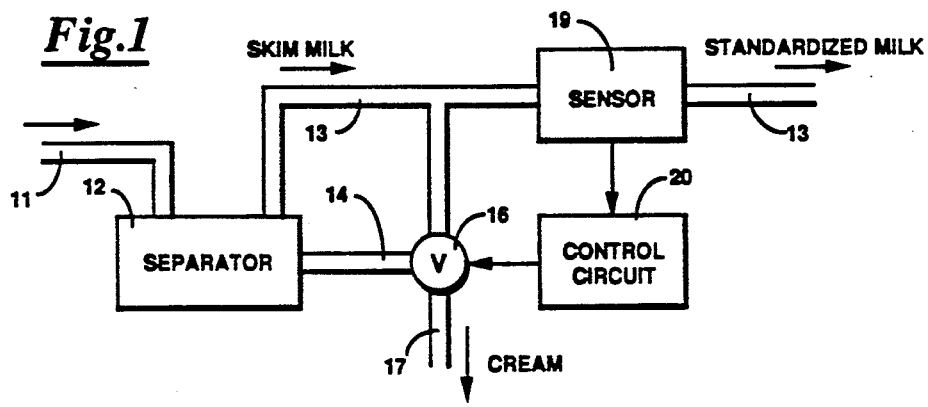
FIG. 1 is a schematic diagram of one embodiment of a system for producing milk having a standardized butterfat content in accordance with the invention.

As illustrated in FIG. 1, raw milk is applied to the input line 11 of a centrifugal separator 12 where it is separated into low fat, or skim, milk and high fat milk, or cream. The low fat milk is delivered to a product output line 13, and the high fat milk is delivered to a cream line 14. A cream control valve 16 has an inlet connected to cream line 14 and outlets connected to product output line 13 and to a cream output line 17. The adjustment of this valve controls the amount of high fat milk, or cream, which is combined with the low fat milk in the product output line, with the portion of the cream which is not delivered to the product output line being discharged through the cream output line.

The product output line passes through an in-line sensor 19 which monitors the butterfat content in the product stream. In one presently preferred embodiment, the sensor is an optical density sensor, and the entire product stream is monitored as it passes through the sensor. Suitable sensors are available from Wedgewood Technology, Inc., San Carlos, Calif., and include Model Nos. AF10-10-TC, AF10-20-TC, and AF10-30-TC. These sensors have stainless steel bodies and housings, with Pyrex windows, and they mount directly on the product output lines and operate at full flow and pressure. They monitor the optical density of the product stream which varies with the butterfat content of the milk. The Wedgewood sensors are particularly suitable since they can resolve small changes in the butterfat content, for example, a change of only 0.005% in a product having a 2% butterfat content.

A control circuit 20 monitors the output signal from sensor 19 and controls the operation of valve 16 to maintain a desired butterfat content in the product stream.

Figure 2:
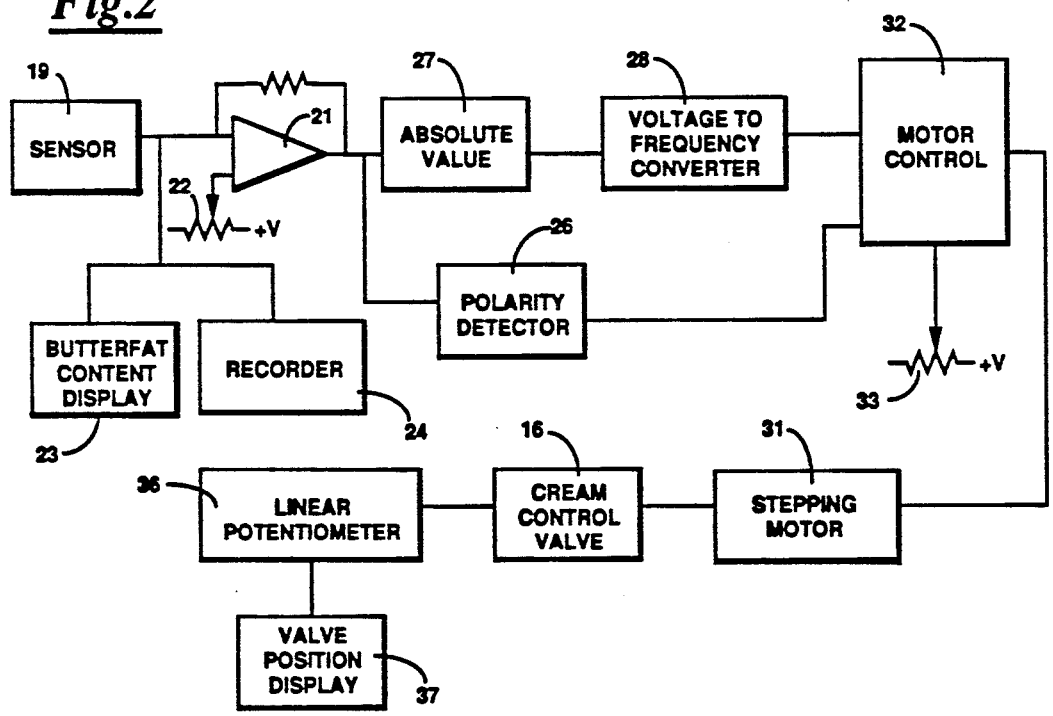
FIG. 2 is a block diagram of the control circuit employed in the embodiment of FIG. 1.

As illustrated in FIG. 2, the output of sensor 19 is connected to one input of a differential amplifier 21, and a reference signal corresponding to the desired butterfat content in the product stream is applied to a second input of this amplifier. The reference signal is provided by a manually adjustable potentiometer 22 connected to a voltage source +V, which permits an operator to set the desired butterfat content. The potentiometer can be provided with a dial (not shown) calibrated in units of butterfat content, e.g. percent, and by setting the potentiometer to the desired butterfat content, the operator sets the level of the reference signal.

The output of sensor 19 is also applied to a digital display 23, which displays the butterfat content of the product stream, and to a recorder 24. Any suitable type of recorder can be employed, and one particularly suitable type of recorder for this purpose is a circular recorder having a chart speed which can be adjusted from 1 to 168 hours per revolution.

The output of differential amplifier 21 is an error signal which consists of a voltage having an amplitude and polarity corresponding to the relative levels of the sensor signal and the reference signal. In one presently preferred embodiment, the sensor signal is a positive voltage having a magnitude which varies between zero and 5 volts, depending on the butterfat content of the milk and the sensitivity or range for which the system is set, and the reference voltage is set midway between the limits of the sensor voltage, e.g., at about 2.5 volts. If the sensor voltage is higher than the reference signal, the error signal is positive, and if the sensor voltage is lower than the reference voltage, the error signal is negative.

The output of amplifier 21 is connected to the inputs of a polarity detector 26 and a circuit 27 which delivers an output voltage corresponding to the absolute value of the error signal. The output of circuit 27 is connected to the input of a voltage to frequency converter 28 which produces an output signal containing a series of pulses which occur at a rate corresponding to the magnitude of the error signal, i.e. to the difference between the monitored butterfat content and the desired content.

Control valve 16 is driven by a stepping motor 31, and the signals from converter 28 and polarity detector 26 are applied to the inputs of a motor controller 32 which drives the stepping motor. The stepping motor thus advances one step in response to each pulse in the control signal from converter 28, and as the butterfat content of the product approaches the desired level, the pulse rate and, hence, the rate at which the valve is adjusted decreases, and the butterfat content approaches the desired level smoothly and gradually without overshoot or hunting. A manually adjustable potentiometer 33 connected to motor controller 32 permits the control valve to be set manually.

A linear potentiometer 36 is operatively connected to the control valve to provide a signal corresponding to the position of the valve. This signal is applied to a display 37 which indicates the position of the valve. This display is helpful to the operator in making certain that the system is set to operate within its normal range.

Operation and use of the system, and therein the method of the invention, can now be described. Potentiometer 22 is set for the desired butterfat content, and the system is turned on to begin processing the raw milk. As the raw milk is separated into low fat milk and high fat milk and a portion of the high fat milk is recombined with the low fat milk in product output line 13, the butterfat content in the product stream is monitored by sensor 19.

Sensor 19 provides an electrical signal which has a magnitude corresponding to the butterfat content, and this signal is compared with the reference signal from potentiometer 22 in differential amplifier 21. The signal produced by this amplifier has a magnitude and a polarity corresponding to the difference between the actual butterfat content in the product stream and the desired content.

Circuit 27 provides an output voltage corresponding to the absolute value, i.e. magnitude, of the error signal from differential amplifier 21, and polarity detector 26 provides a signal which indicates the polarity of the error signal. The absolute value signal from circuit 27 is converted to a pulse train or series of pulses by voltage to frequency converter 28. The pulses occur at a rate proportional to the magnitude of the error signal, i.e. to the difference between the actual butterfat content and the desired content.

The pulse signal from converter 32 and the polarity signal from detector 26 are applied to motor controller 32 which causes the stepping motor 31 to advance one step in response to each pulse in the pulse train and in the direction specified by the polarity signal. Each time the stepping motor steps, it adjusts the cream control valve by a fixed increment to increase or decrease the amount of high fat milk delivered to the product output line. When the monitored butterfat content differs by a larger amount from the desired fat content, the pulses occur at a higher rate, and the amount of cream added is increased or decreased more rapidly than it is when the content approaches the desired level. As the content gets closer to the desired level, the pulses occur less frequently, and the adjustment in the amount of cream added is made gradually and smoothly without overshoot or hunting about the desired level.

Visual indications of the butterfat content of the product stream and the position of the cream control valve 16 are provided by displays 23 and 37, and the butterfat content is recorded continuously by recorder 24.

Figure 3:
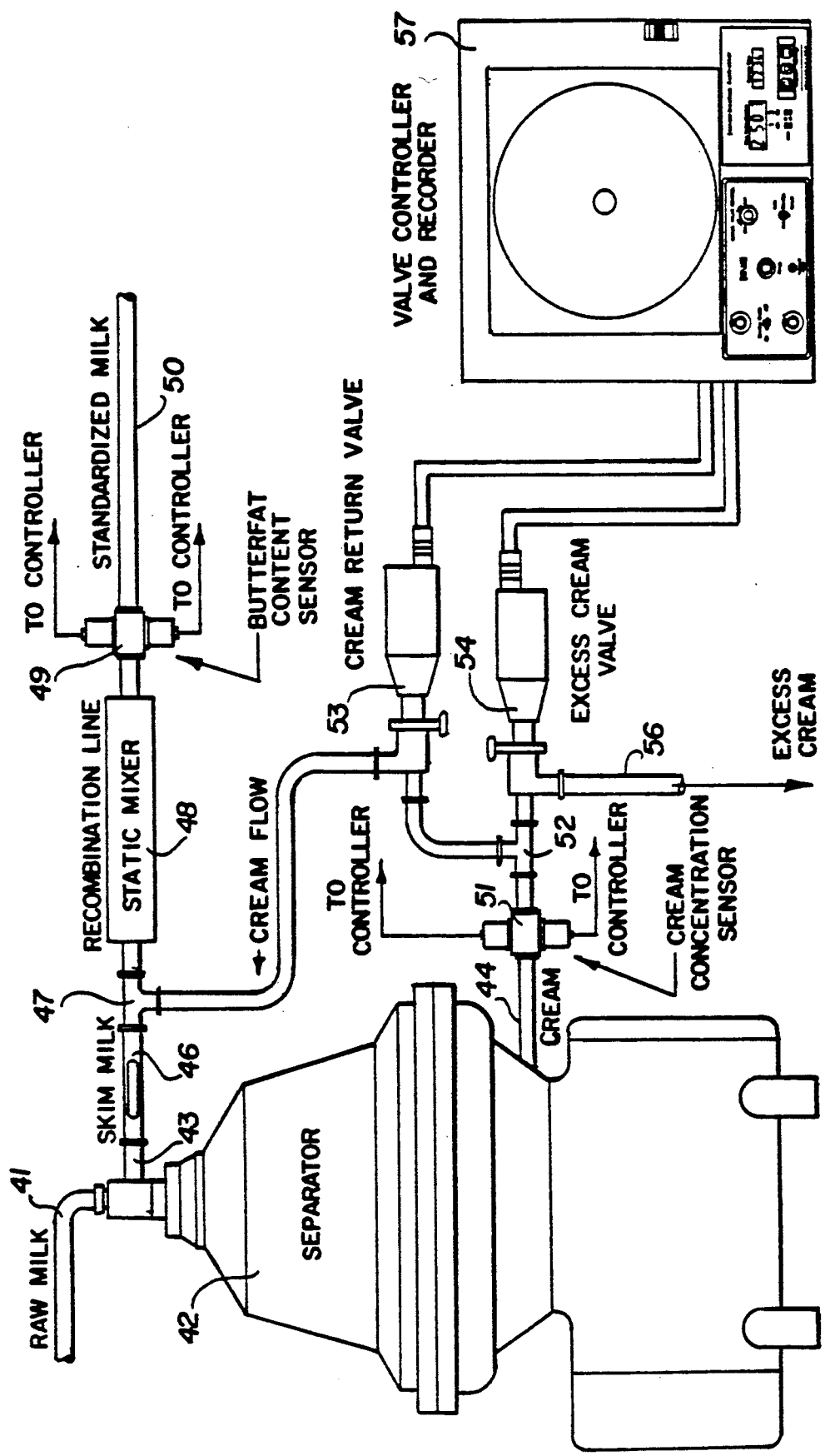
FIG. 3 is a schematic diagram of another embodiment of a system for producing milk having a standardized butterfat content in accordance with the invention.
Figure 4A:
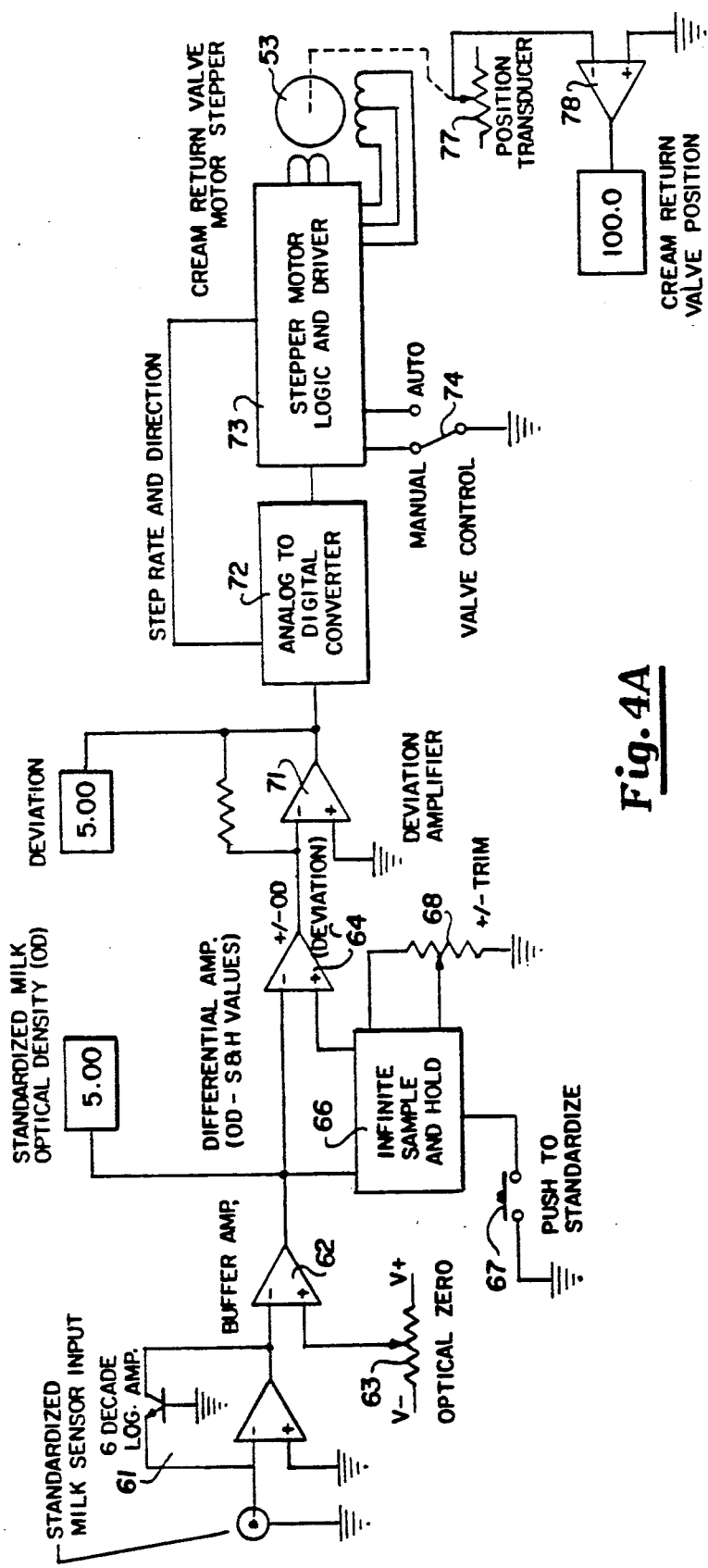
FIGS. 4A and 4B are block diagrams of control circuits for use in the embodiment of FIG. 3.
Figure 4B:
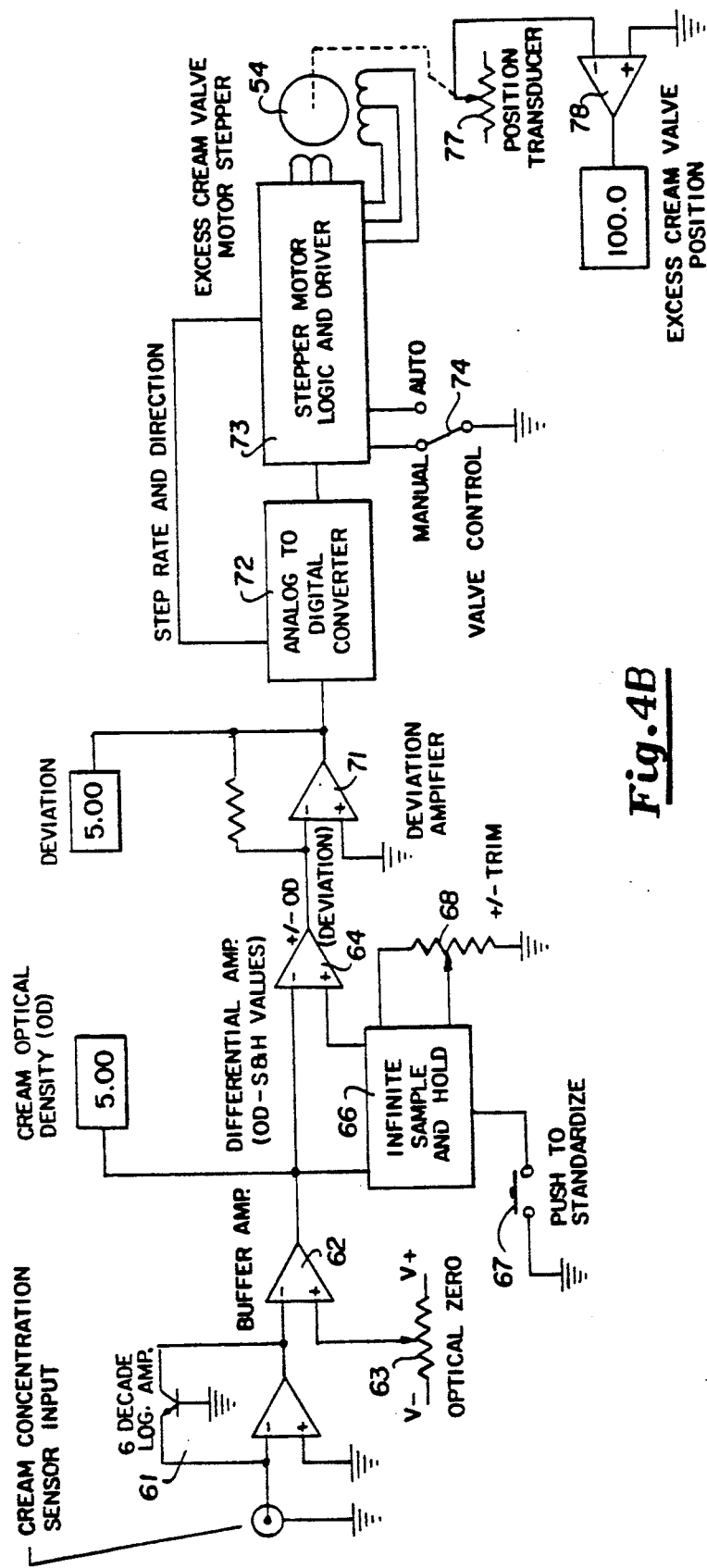
Figure 5:
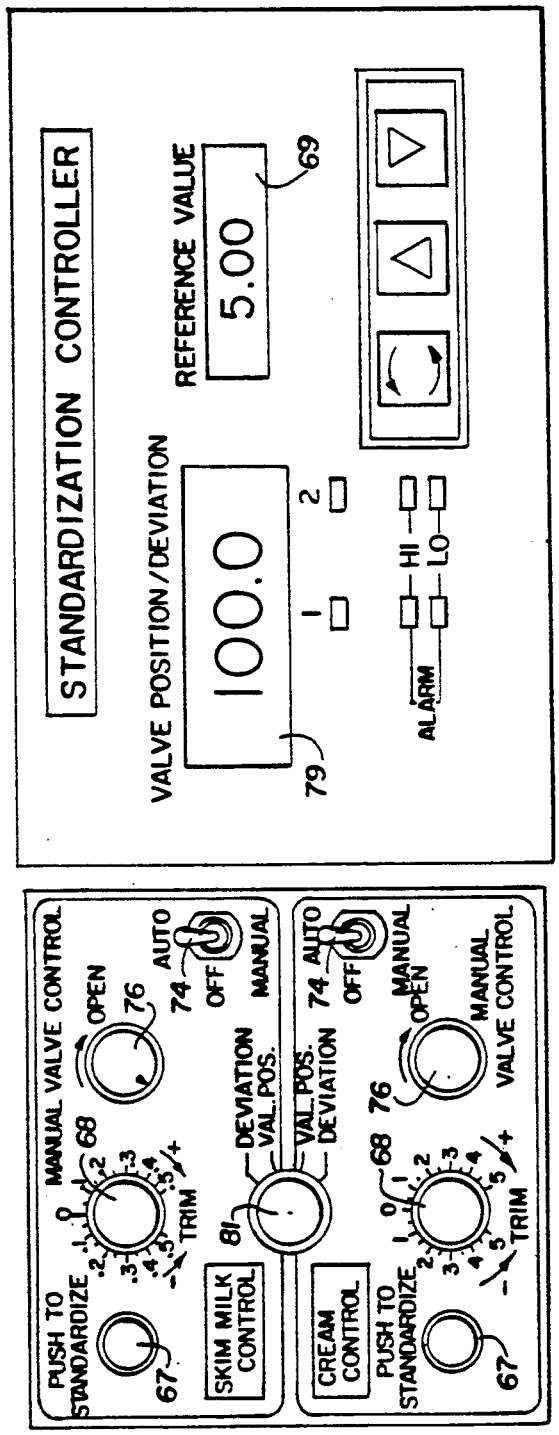
FIG. 5 is a front elevational view of the control panel of the controller in the embodiment of FIG. 3.

In the embodiment illustrated in FIGS. 3-5, means is provided for controlling the butterfat content of the excess cream output as well as the butterfat content of the standardized milk product. As in the embodiment of FIG. 1, raw milk is applied to the input line 41 of a centrifugal separator 42 where it is separated into low fat milk (skim milk) and high fat milk (cream). The separator has a skim milk outlet 43 and a cream outlet 44. The skim milk passes through a sight glass line 46 to a tee fitting 47, and from the tee fitting to a static mixer or recombination line 48 where a controlled amount of cream is added back into the skim milk to produce a standardized milk product having the desired butterfat content. The product stream passes through an in-line sensor 49 similar to sensor 19. The entire product stream passes through the sensor, and the butterfat content is determined from the optical density of the stream. From the sensor, the standardized milk product is delivered to an output line 50.

The cream from the separator passes through a similar sensor 51 to a tee fitting 52, and from the tee fitting to a pair of control valves 53, 54. The outlet of valve 53 is connected to an inlet of the tee fitting 47 in the standardized milk line, and the outlet of valve 54 is connected to an excess cream output line 56. In a presently preferred embodiment, valves 53, 54 are electrically operated micrometer valves, and the operation of these valves is controlled by a controller 57 with a recorder similar to recorder 24. The controller receives input signals from sensors 49, 51.

Valve 53 controls the butterfat content in the standardized milk product, and valve 54 controls the butterfat content in the excess cream. There is, however, some interaction between the two valves, and an increase in one valve may require a decrease in the flow through the other to maintain a desired output consistency. Thus, for example, an increase in the flow through the cream return valve 53 may require a decrease in the flow through the excess cream valve 54 to maintain the proper cream discharge consistency.

As illustrated in FIGS. 4A and 4B, the controller has separate control channels 58, 59 for the two control valves. The two channels are similar, and like reference numerals designate corresponding components in them. Channel 58 monitors the signals from milk product sensor 49 and controls the operation of cream return valve 53, and channel 59 monitors the signals from cream sensor 51 and controls the operation of excess cream valve 54.

Each of the control channels has a logarithmic amplifier 61 to which the signals from the sensor associated therewith are applied. The output of the logarithmic amplifier is connected to one input of a buffer amplifier 62 which has a second input to which an adjustable zeroing voltage is applied by a potentiometer 63. The signal at the output of the buffer amplifier in channel 58 corresponds to the optical density and butterfat content of the standardized milk product in output line 50, and the signal at the output of the buffer amplifier in channel 59 corresponds to the optical density and butterfat content of the cream from the cream outlet 44 of the separator.

The signal from amplifier 62 is applied to one input of a differential amplifier 64 and to the input of a sample and hold circuit 66, and the output of the sample and hold circuit is applied to a second input of the differential amplifier. A manually operable pushbutton switch 67 mounted on the front panel of the controller is connected to the sample and hold circuit for conditioning that circuit to store a value corresponding to the optical density or butterfat content of the milk product or cream at the time the switch is closed. A trimming potentiometer 68 is connected to the sample and hold circuit and is adjustable from the front panel of the controller. The reference level stored by the sample and hold circuit is displayed by a display 69 on the front panel of the controller.

The signal at the output of differential amplifier 64 represents the deviation of the butterfat content of the standardized milk or the cream from the desired value. This signal is amplified by an amplifier 71 and converted to digital form by an analog-to-digital converter 72, and the digital signal is applied to a logic circuit and driver 73 for the stepping motor for the valve controlled by the channel, i.e. cream return valve 53 or excess cream valve 54. A panel mounted switch 74 is connected to the logic circuit and driver for switching between manual and automatic modes, and a control 76 is mounted on the panel for setting the position of the valve in the manual mode. The position of the valve in either mode is monitored by a linear potentiometer 77 or other suitable position transducer, and the signal from the position transducer is amplified by an amplifier 78.

A display 79 is mounted on the front panel of the controller for indicating the deviation of the milk product and the cream from the reference levels and the positions valves 53, 54. A switch 81 on the panel selectively applies the signals from deviation amplifiers 71 and valve position amplifiers 78 to the display for this purpose.

In operation, valves 53, 54 are set manually to provide the desired butterfat content in the milk product stream and in the cream, at which point the sample and hold circuits are actuated to store these values. Fine adjustments can be made by zeroing potentiometers 63 and by trimming potentiometers 68, and the system can be set to use the current butterfat content of either the milk product or the cream as a reference value or standard at any time by pressing the appropriate switch 67.

In the automatic mode, the deviation signals from amplifiers 71 drive the stepping motors associated with the control valves to eliminate any deviation from the values which have been set.

By providing separate controls for the standardized milk product and for the cream, the system provides more precise control over the product stream than a system which controls only the amount of cream which is recombined with the skim milk.

The invention has a number of important features and advantages. The system is extremely easy to use, and it is also extremely accurate. The butterfat content in the product stream can be set simply by adjusting a potentiometer, and thereafter the system will automatically adjust the fat content to this level and maintain it there. The system approaches the setpoint gradually, with the rate of adjustment decreasing as the desired level gets closer. This provides a smooth adjustment and effectively eliminates overshoot and hunting about the setpoint. By using an optical density sensor and monitoring the entire product output stream, a substantially greater accuracy is obtained than in systems in which only a portion of the product is monitored. This system can, for example, maintain an accuracy of 0.005% with a butterfat content of 2%. The system is easily installed in existing milk processing systems, and the control panel can be located remotely of the processing system, e.g. up to several hundred feet away.

The invention does not require any of the metering pumps or proportional control valving found in many prior art systems, and it operates on an on-line basis, providing very fast, essentially real time, control.

While the invention has been described with specific reference to a system and method for controlling the butterfat content in milk, it is applicable to other products as well, including fruit juice, beer and other fluid products having separable constituents.

It is apparent from the foregoing that a new and improved system and method have been provided for controlling the content of a fluid product such as milk. While only certain presently preferred embodiments have been described in detail, as will be apparent to those familiar with the art, certain changes and modifications can be made without departing from the scope of the invention as defined by the following claims.

I claim:

1. In a system adapted to produce the butterfat content of a standardized milk product produced by combining low fat milk and high fat milk: means for providing a first reference signal corresponding to a desired butterfat content for the standardized milk product and a second reference signal corresponding to a desired butterfat content for the high fat milk, a sensor adapted to provide an output signal which varies in accordance with the butterfat content of milk monitored thereby, means for delivering all of the standardized milk product to the sensor so that the output signal varies in accordance with the butterfat content of the product, means for monitoring the high fat milk and providing a signal which varies in accordance with the butterfat content of the high fat milk, means including a valve responsive to the first reference signal and to the output signal from the sensor for combining a portion of the high fat milk with the low fat milk at a location upstream of the sensor to control the butterfat content of the standardized product, and valve means responsive to the second reference signal and to the butterfat content signal for the high fat milk for controlling delivery of the high fat milk to an output line.

2. The system of claim 1 wherein the sensor comprises an optical density sensor through which all of the product passes.

3. The system of claim 1 wherein the means for monitoring the high fat milk comprises an optical density sensor, and means for passing all of the high fat milk through the optical density sensor.

4. The a method of controlling the butterfat content of a standardized milk product produced by combining low fat milk and high fat milk, the steps of: providing a first reference signal corresponding to desired butterfat content for the standardized milk product and a second reference signal corresponding to the desired butterfat content for the high fat milk, delivering all of the standardized milk product to a sensor to provide an output signal which varies in accordance with the butterfat content of the product, monitoring the high fat milk and providing a signal which varies in accordance with the butterfat content of the high fat milk, combining a portion of the high fat milk with the low fat milk at a point upstream of the sensor in accordance with the first reference signal and the the output signal from the sensor to control the butterfat content of the standardized product, and controlling delivery of the high fat milk to an output line in accordance with the second reference signal and the butterfat content signal for the high fat milk.

5. The method of claim 4 wherein all of the standardized milk product is passed through an optical density sensor to provide the output signal.

6. The method of claim 4 wherein the high fat milk is monitored by passing all of the high fat milk through an optical density sensor.

7. In a system adapted to produce a standardized milk product having a desired butterfat content from a stream of raw milk: a separator for separating the raw milk into skim milk and a cream, a product line, means for delivering the skim milk to the product line, a cream return valve connected between the separator and the product line for recombining a controlled amount of cream with the skim milk to form the standardized milk product in the product line, means for monitoring the butterfat content of all of the standardized milk product in the product line at a location downstream of where the cream is recombined with the skim milk and controlling the cream return valve to maintain the butterfat content of the standardized product at a predetermined level, an excess cream valve controlling delivery of cream from the separator to a cream output line, and means for monitoring the butterfat content of the cream and controlling the excess cream valve to maintain the butterfat content of the cream in the output line at a desired level.

8. The system of claim 7 wherein the means for monitoring the butterfat content of the standardized milk product comprises an optical density sensor connected to the product line so that all of the product in the product line passses through the sensor.

9. The system of claim 7 wherein the means for monitoring the butterfat content of the cream comprises an optical density sensor connected to the separator so that all of the cream from the separator passes through the sensor.

10. In a method of producing a standardized milk product having a desired butterfat content from a stream of raw milk, the steps of: separating the raw milk into skim milk and cream, delivering the skim milk to a product line, delivering a portion of the cream through a cream return valve to the product line for recombination with the skim milk to form the standardized milk product in the product line, monitoring the butterfat content of all of the standardized milk product in the product line at a location downstream of where the cream is delivered to the line and controlling the cream return valve to maintain the butterfat content of the standardized product in the line at a redetermined level, delivering the remainder of the cream through an excess cream valve to a cream output line, and monitoring the butterfat content of the cream and controlling the excess cream valve to maintain the butterfat content of the cream in the output line at a desired level.

11. The method of claim 10 wherein the butterfat content of the standardized milk product is monitored by passing all of the product through an optical density sensor.

12. The method of claim 10 wherein the butterfat content of the cream is monitored by passing all of the cream from the separator through an optical density sensor.

13. In a system adapted to produce the butterfat content of a standardized milk product produced by combining low fat milk and high fat milk: means for providing a first reference signal corresponding to a desired butterfat content for the standardized milk product and a second reference signal corresponding to a desired butterfat content for the high fat milk, means for monitoring the milk product and providing an output signal which varies in accordance with the butterfat content of the milk product, a sensor adapted to provide a signal which varies in accordance with the butterfat content of milk monitored thereby, means for delivering all of the high fat milk to the sensor so that the signal provided by the sensor varies in accordance with the butterfat content of the high fat milk, means including a valve responsive to the first reference signal and to the output signal for combining a portion of the high fat milk with the low fat milk at a location upstream of the sensor to control the butterfat content of the standardized product, and valve means responsive to the second reference signal and to the signal from the sensor for controlling delivery of the high fat milk to an output line.

14. The system of claim 13 wherein the sensor comprises an optical density sensor, and means for passing all of the high fat milk through the optical density sensor.

15. In a method of controlling the butterfat content of a standardized milk product produced by combining low fat milk and high fat milk, the steps of: providing a first reference signal corresponding to desired butterfat content for the standardized milk product and a second reference signal corresponding to the desired butterfat content for the high fat milk, monitoring the standardized milk product and providing a milk product signal which varies in accordance with the butterfat content of the standardized milk product, delivering all of the high fat milk to a second to provide an output signal which varies in accordance with the butterfat content of the high fat milk, combining a portion of the high fat milk with the low fat milk at a point upstream of where the standardized milk product is monitored in accordance with the first reference signal and the milk product signal to control the butterfat content of the standardized product, and controlling delivery of the high fat milk to an output line in accordance with the second reference signal and the butterfat content signal for the high fat milk.

16. The method of claim 15 wherein all of the high fat milk is passed through an optical density sensor to provide the output signal.

17. In a system adopted to produce a standardized milk product having a desired butterfat content from a stream of raw milk: a separator for separating the raw milk into skim milk and cream, a product line, means for delivering the skim milk to the product line, a cream return valve connected between the separator and the product line for recombining a controlled amount of cream with the skim milk to form the standardized milk product in the product line, means for monitoring the butterfat content of the standardized milk product in the product line at a location downstream of where the cream is recombined with the skim milk and controlling the cream return valve to maintain the butterfat content of the standardized product at a predetermined level, an excess cream valve controlling delivery of cream from the separator to a cream output line, and means for monitoring the butterfat content of all of the cream from the separator and controlling the excess cream valve to maintain the butterfat content of the cream in the output line at a desired level.

18. The system of claim 17 wherein the means for monitoring the butterfat content of the cream comprises an optical density sensor connected to the separator so that all of the cream from the separator passes through the sensor.

19. In a method of producing a standardized milk product having a desired butterfat content from a stream of raw milk, the steps of: separating the raw milk into skim milk and cream, delivering the skim milk to a product line, delivering a portion of the cream through a cream return valve to the product line for recombination with the skim milk to form the standardized milk product in the product line, monitoring the butterfat content of the standardized milk product in the product line at a location downstream of where the cream is delivered to the line and controlling the cream return valve to maintain the butterfat content of the standardized product in the line at a predetermined level, delivering the remainder of the cream through an excess cream valve to a cream output line, monitoring the butterfat content of all of the cream from the separator, and controlling the excess cream valve to maintain the butterfat content of the cream in the output line at a desired level.

20. The method of claim 19 wherein the butterfat content of the cream from the separator is monitored by passing all of the cream from the separator through an optical density sensor.

* * * * *